United States Patent [19]
Shukla et al.

[11] Patent Number: 5,922,186
[45] Date of Patent: Jul. 13, 1999

[54] STAINING, DE-STAINING AND QUANTIFICATION OF PROTEINS BY COOMASSIE-BLUE AND RELATED DYES

[76] Inventors: Ashok K. Shukla; Amita M. Shukla, both of 10423 Popkins Ct., Woodstock, Md. 21163

[21] Appl. No.: 08/903,456

[22] Filed: Jul. 28, 1997

[51] Int. Cl.[6] .................. G01N 27/26; G01N 27/447
[52] U.S. Cl. ........................... 204/606; 204/462
[58] Field of Search .................. 204/462, 463, 204/606, 613, 615, 616, 456

[56] References Cited

U.S. PATENT DOCUMENTS

| | | | |
|---|---|---|---|
| 4,021,324 | 5/1977 | Delony et al. | 204/463 |
| 4,357,174 | 11/1982 | Rushbrook et al. | 134/10 |
| 4,750,506 | 6/1988 | Olexa | 134/20 X |

*Primary Examiner*—William H. Beisner
*Assistant Examiner*—John S. Starsiak, Jr.

[57] ABSTRACT

The present invention presents a novel method for both staining electrophoresis gels, as well as removing the background dye during de-staining. This novel and simple pad-based technique minimizes solvent consumption, is environmentally friendly, and does not leave any solid residues on the gel. Furthermore, a novel method for the quantitative and qualitative determination of protein concentration in solution is also presented. This method is simple, easy-to-use and has an easily visible color change from clear to blue in the presence of protein.

6 Claims, 7 Drawing Sheets

STAINING, DE-STAINING AND QUANTIFICATION OF PROTEINS BY COOMASSIE-BLUE AND RELATED DYES

FIELD AND BACKGROUND OF THE INVENTION

The separation of biological molecules such as proteins, peptides and glycoproteins is performed by gel electrophoresis. The gels, in which the molecules are embedded after electrophoresis, are stained with coomassie-blue dye to visualize the protein bands. After staining of the protein bands, the excess dye is removed by washing the gel repeatedly with de-stain solution. The present invention presents a novel method for both staining electrophoresis gels, as well as removing the background dye during de-staining. Furthermore, a novel method for the quantitative determination of protein concentration in solution is also presented.

FIELD OF THE INVENTION

Staining and de-staining of protein bands in electrophoresis gels; quantification of protein concentration in solution by utilizing coomassie blue.

BACKGROUND OF THE INVENTION

The process of gel electrophoresis for proteins depends on the movement of molecules along an electric field on the basis of properties such as size, charge and pH. The protein samples are placed in a row of small compartments on one side of a gel. The gel typically consists of porous materials such as agarose or polyacrylamide, and is suspended in an electrolytic medium.

Upon application of an electric current, the molecules in the different compartments move in their individual lanes. The distance of movement depends upon the qualities of a specific protein, as well as the buffer medium and pore size of the gel. At the termination of electrophoresis, the molecules of each compartment exist as a series of one or more bands along the length of a lane.

The first steps, immediately after the separation of proteins, are the fixation and visualization of the individual bands. One of the most common dyes used for this process is coomassie blue. During the staining process, the dye, in addition to binding to the protein bands, also diffuses into the entire gel. This excess dye is removed by washing the gel with a de-stain solution, which contains either acetic acid or alcohol, or a combination of both. The de-stain solution is replaced from time to time, and the gel is usually placed on a stirrer to facilitate the diffusion of the non-bound dye out of the gel and into the surrounding solution.

Some methods have been developed to decrease the de-staining time for gels. One of the most commonly applied procedures is to increase the volume of de-stain solution during each wash or to increase the number of washes. However, this process is tedious, time consuming, and requires larger quantities of the de-stain solution.

Other methods involve adding active charcoal (Rushbrook et. al. U.S. Pat. No. 4,357,174) or ion-exchange resin (Delony et. al., U.S. Pat. No. 4,021,324) to the gel. However, the Rushbrook procedure leaves charcoal residues on the gel, while the Delony technique requires passing an electric current through the gel, which may also disturb the protein bands and move them from their original positions.

An additional method requires a specially designed container in which gels are placed for de-staining (Chu, U.S. Pat. Nos. 4,702,266 and 4,705,056). In this technique the size of gels to be de-stained is limited to the size of the container.

Another method, which is commercially marketed by NOVEX, Inc., utilizes a colloidal suspension of a dye absorbing material. However, the absorbing material's color changes to blue as it absorbs the excess dye from the gel, which makes the visualization of the gel difficult without removal of the absorbing material. Also, residues of the material are often left on the gel itself, and may interfere with photography and disturb the analysis.

The present invention provides a novel and simple method for the removal of dye from gels and the visualization of protein bands. This method does not require any special systems or equipment. Furthermore, this technique also minimizes solvent consumption, is environmentally friendly, and does not leave any solid residues on the gel.

Additionally, the present invention describes a method for the qualitative and quantitative determination of protein concentration. This method is simple, easy-to-use, and does not require high acid concentrations as do other procedures such as the Bradford assay (Bradford, U.S. Pat. No. 4,023,933). Also, the color change, indicating the presence of protein is from clear to blue and thus easy to visualize and assay. In the Bradford technique, on the other hand, the color change is from brown to blue-green. Furthermore, in the present invention, the color with which the protein is labeled is very stable for longer periods of time, and, unlike the Bradford assay, the test results do not need to be read in a short frame of time.

SUMMARY OF THE INVENTION

It is an object of the present invention to provide a simple method for coomassie-blue staining and subsequent de-staining of slab, round or other types of gels. The present technique is easy to use, relatively faster, and does not require any additional equipment.

Another aspect described herein is a simple and straight-forward method for qualitative and quantitative determination of protein concentration in solution.

The de-staining system described herein is based on the absorptive capabilities of a foam pad that is placed in a container with the gel. The foam pad absorbs coomassie blue from the aqueous solution, which may or may not contain acetic acid and/or ethanol in a specific concentration ratio. As the concentration of the dye decreases in the solution surrounding the gel, the dye continues to diffuse out of the gel, and the foam pad subsequently absorbs it. This pad-based process thus accelerates the diffusion process of dye out of the gel and there is no need to change the surrounding solution.

Similarly, a gel can also be stained by using foam pads soaked in supersaturating levels of coomassie dye. When a gel piece is placed between two such pads soaked with dye, only the protein of the gel is stained. In this process the dye stains the background of the gel less intensely, thus facilitating the visualization and de-staining of the gel.

Another application of the coomassie blue-soaked pad is the qualitative and quantitative determination of protein concentration. Since the pad does not bind protein, when a protein solution is brought in contact with a coomassie blue-soaked pad, the dye will bind to the protein in solution. The concentration of blue color in the solution is directly proportional to the protein concentration in solution. A control solution, which does not contain any protein, will be clear since all the dye remains bound to the pad.

The various features of novelty that characterize the invention are pointed out with particularity in the claims annexed to and forming a part of this disclosure. For a better understanding of the invention, its advantages and objects, reference is made to the accompanying drawing and descriptive matter in which a preferred embodiment of the invention is illustrated.

BRIEF DESCRIPTION OF THE DRAWINGS

The foregoing and still other objects of this invention will become apparent, along with various advantages and features of novelty residing in present embodiments, from study of the following drawings, in which.

DESCRIPTION OF THE PREFERRED EMBODIMENTS

The foam pad described in the present invention is a natural or synthetic foam that can absorb water and has an affinity for organic molecules. For instance, Polyvinyl alcohol (PVA) and related foams hold such properties. Such foams are composed of a very porous material that has high water absorbing properties and a high surface volume. This material absorbs organic dyes quantitatively. For example, coomassie blue dye can be absorbed quantitatively from a solution of commassie blue dye in an acidic solution which may or may not contain alcohol (e.g. ethanol, methanol, propanol, isopropanol etc). This concept has been utilized herein to develop new methods for staining and de-staining electrophoresis gels, and for creating the novel technique for protein concentration determination in a solution.

Figure 1:
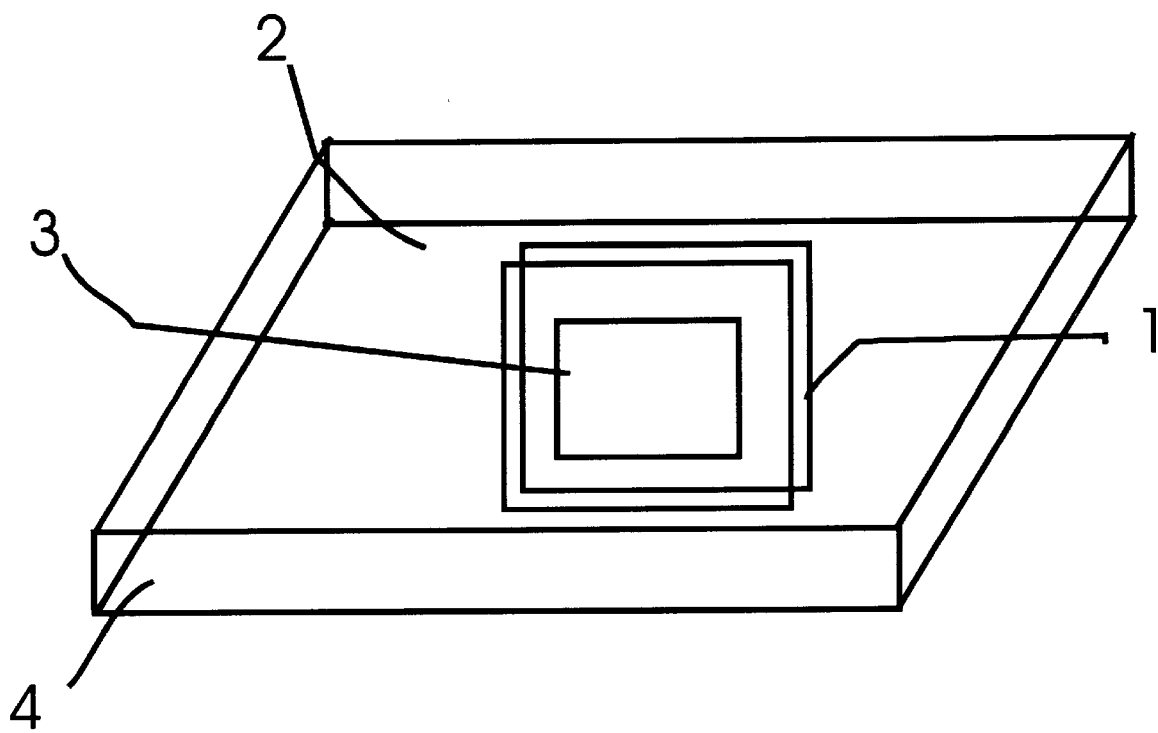
FIG. 1 is an expanded view of the staining pads and gel in a gel tray.

Staining the gel:

A foam piece is soaked in a solution of coomassie blue in ethanol with acetic acid. After electrophoresis has been performed on a gel (3), the gel piece is placed between two coomassie-soaked foam pads (1) as can be seen in FIG. 1. The coomassie dye diffuses from the pads (1) to the gel (3) and, depending upon the conditions under which staining is performed, the gel is stained in a time frame of 20 minutes to a few hours. In many instances the dye binds to the protein bands much more efficiently than it does to the background of the gel, making visualization of the bands much easier.

Other staining techniques typically stain the gel in a uniformly deep blue color. The lower concentration of coomassie dye in the gel background, resulting from the staining technique of this invention, also speeds up the de-staining process if indeed it needs to be performed, since there is a lower intensity of dye to be eliminated from the gel.

A further advantage of using these ready-made staining pads is that there is no need to prepare a staining solution and or place the gel in a separate staining tank. Also, the repetitive pouring and removal of solutions on the gel often damages or breaks the gel. Also, the staining technique described in this invention permits viewing of the gel in the tray (4) anytime during the staining process whereas, it is difficult and tedious to view a gel in the staining solution.

Heating the pad, or warming it for a short duration in a microwave oven can further accelerate the staining process described by this invention. The solution (2) in which the gel and foam pads are placed may contain alcohol, acid, or a combination of the two chemicals. Another method for accelerating the staining process is the application of an electric current between the two foam pads.

Figure 2:
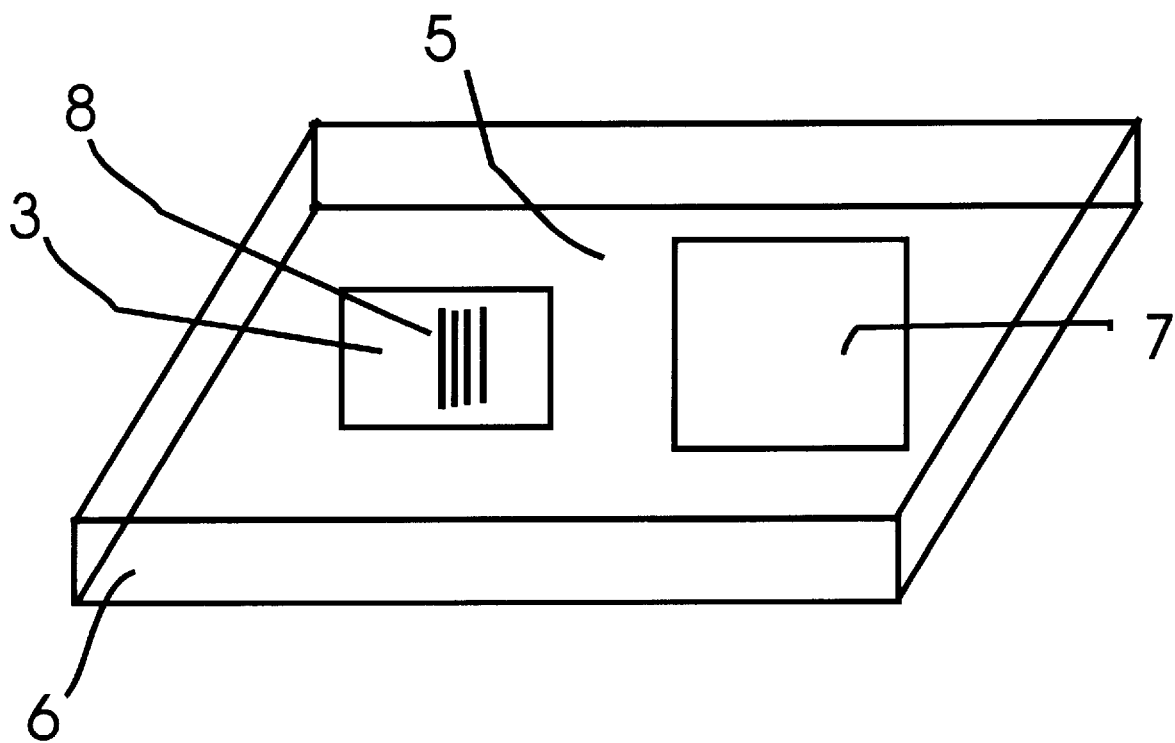
FIG. 2 is an expanded view of the de-staining pad and a gel in a gel tray.

De-staining of the Gel:

As can be seen in FIG. 2, once an electrophoresis gel has been stained, either by the method described above or by placing the gel (3) in a staining container, the gel is placed in a de-staining tray (6). This tray contains a de-staining solution (2). A piece of foam pad (7) is then placed in the same tray. The entire tray is then placed on a shaker or similar device that moves or stirs it very gently for a specific time duration.

As the excess dye diffuses from the gel (3) into the surrounding solution (5), the de-staining foam pad absorbs it. The color of the pad (7) changes from white to blue as the concentration of coomassie blue it has absorbed increases. At the same time, the color of the surrounding solution (5) in the tray changes from blue to clear.

One of the main advantages of this invention is that there is no need to change the buffer solution in the gel tray (6) which helps conserve solvent, minimizes toxic waste, and makes this process very environmentally friendly. The de-staining process may also be enhanced by heating the foam pad or warming it in a microwave oven for a short duration of time. At the end of the de-staining process, the protein bands (8) are clearly visible in blue and the background of the gel is colorless.

Figure 3:
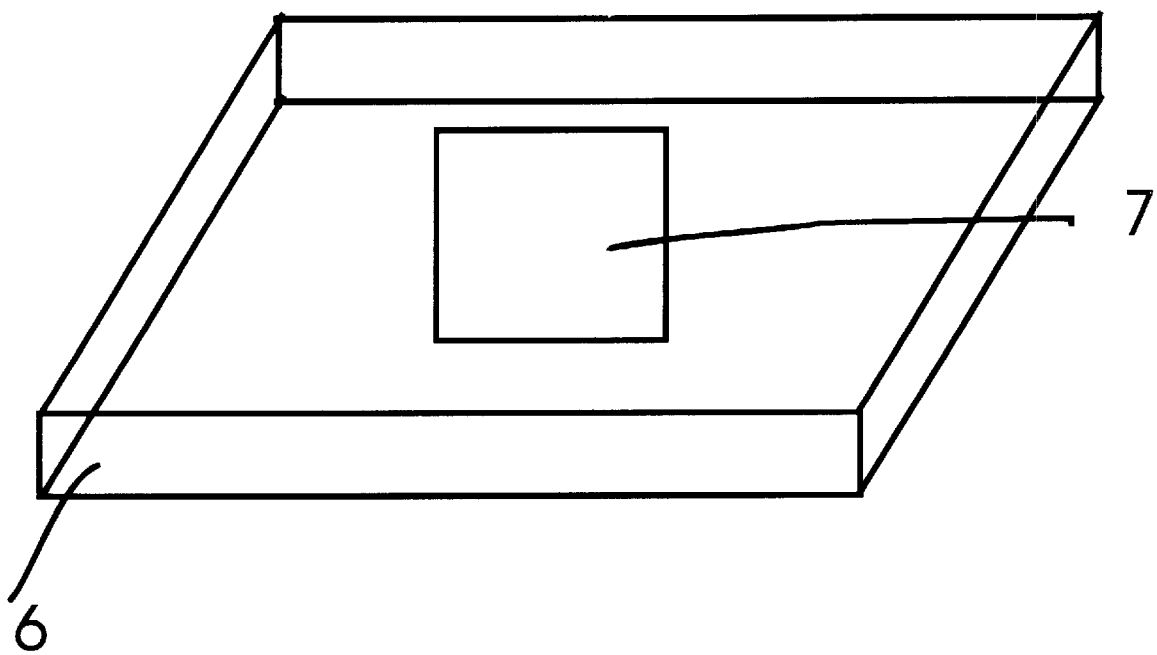
FIG. 3 is an expanded view of a pad affixed to the bottom of a gel tray.

The dye is entirely absorbed by the pad, which may be made of any material that effectively binds coomassie blue, and may be shaped or sized for maximum absorption. As is shown in FIG. 3, the pad (7) may also be embedded in or affixed to the bottom of the gel tray (6). Using this modification, disposable gel trays can be made for one-time applications.

Figure 4:
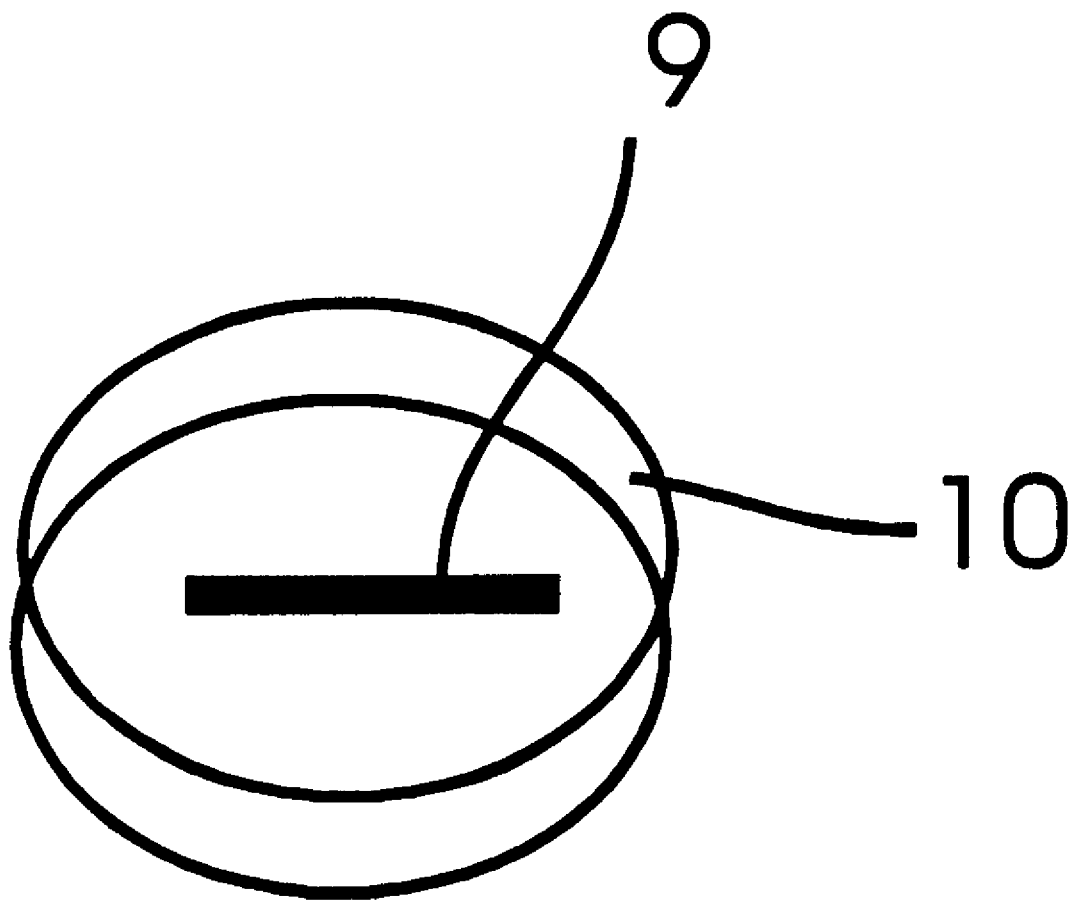
FIG. 4 is an expanded view of a circular pad which contains a magnet in it.

Also, as shown in FIG. 4, a magnet (9) can be inserted into a circular pad (10). This eliminates the need for a shaker since the gel tray (6) can be placed directly on a magnetic stirrer plate. This magnetic stirrer, which is readily available in most labs, will rotate the pad and thereby circulate the buffer, which in turn serves to reduce the duration of the de-staining process. The centrifugal force of the moving pad pushes the de-staining solution into the pad and out of the gel. As the blue solution enters the pad, the dye will be absorbed and the colorless solution will diffuse out.

Figure 7:
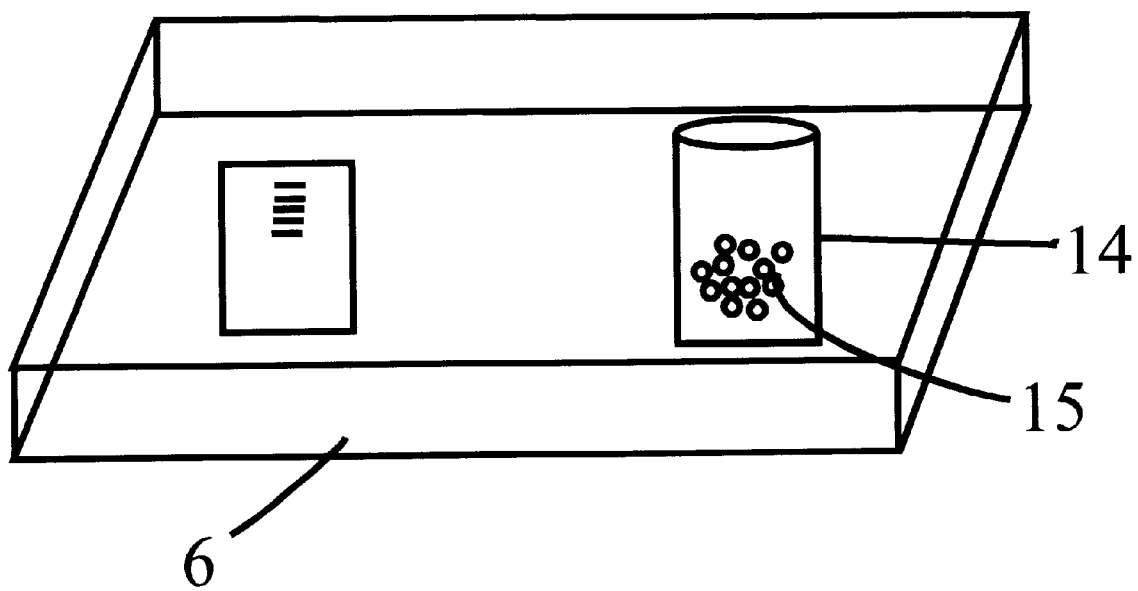
FIG. 7 is an expanded view of the bag made by folding the pad and containing a de-staining material.

As shown in FIG. 7, the de-staining process can also be performed by making bags (14) of the same material as the de-staining pad, which can then be filled with active charcoal (15), ion-exchange resin or other materials that absorb the dye and enhance dye removal.

Qualitative and quantitative protein determination:

Foam pieces soaked in coomassie blue are washed with water until further washes release no more blue color. A small piece of this foam is placed in a solution containing protein. When the container with the protein solution and foam is then shaken or vortexed lightly, the solution turns blue. The intensity of the color in the solution depends upon the concentration of protein present. A control solution that does not contain any protein remains colorless even after the suspension of the coomassie blue stained foam in it.

Figure 5:
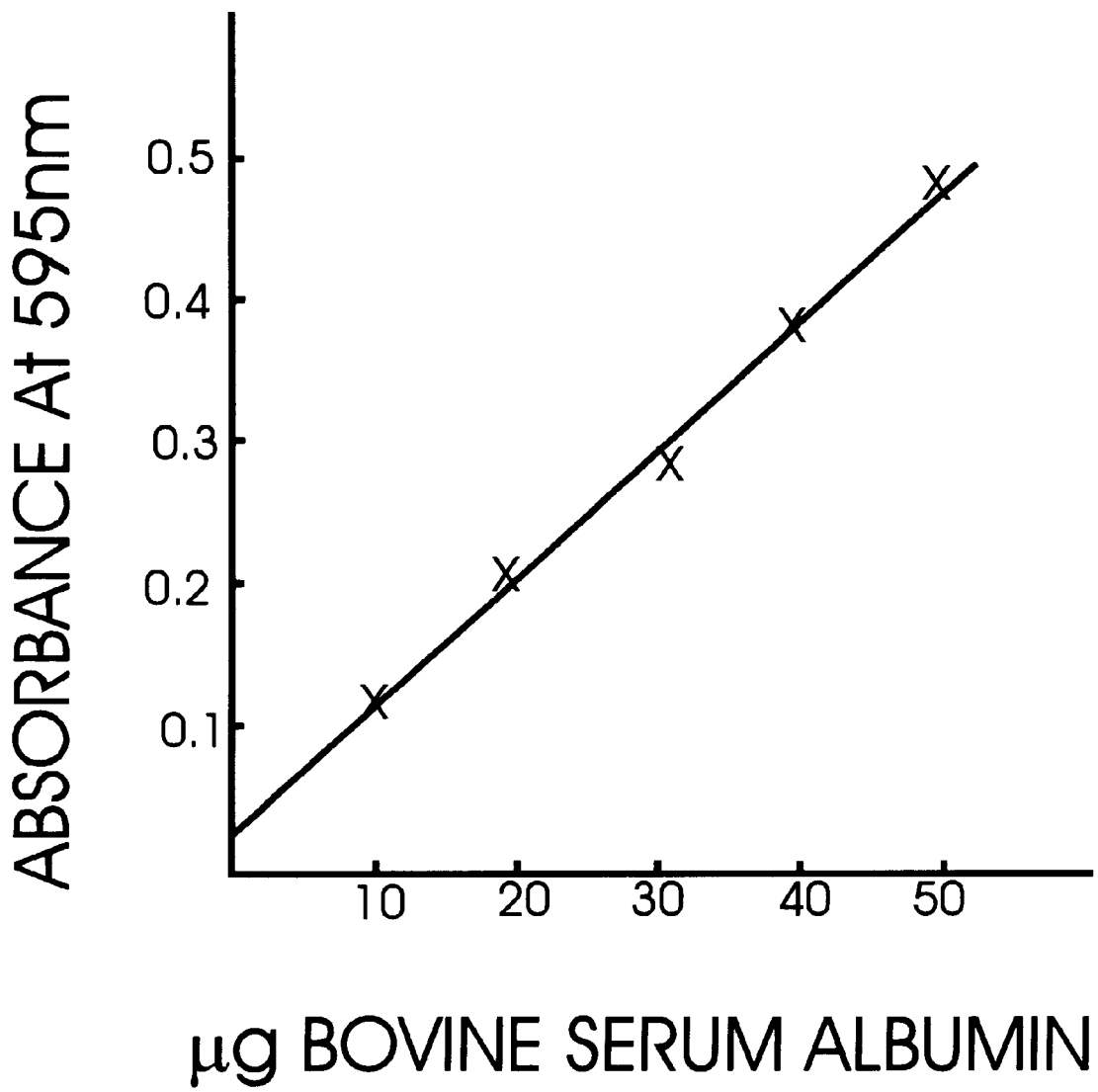
FIG. 5 is a standard curve of protein concentration determination by the assay method described in herein.

FIG. 5 shows a curve for the concentration of bovine albumin in solution versus absorption by photometer at 595 nm. This curve shows that this assay method is linear for the concentrations used under this application. The foam does not absorb the proteins in the solution.

This method for assaying protein concentration has a number of advantages over the earlier method described by Bradford et al. (U.S. Pat. No. 4,023,933) because the color change described by this invention is from clear to blue which is more distinct than the Bradford color change from brown to blue-green.

Figure 6:
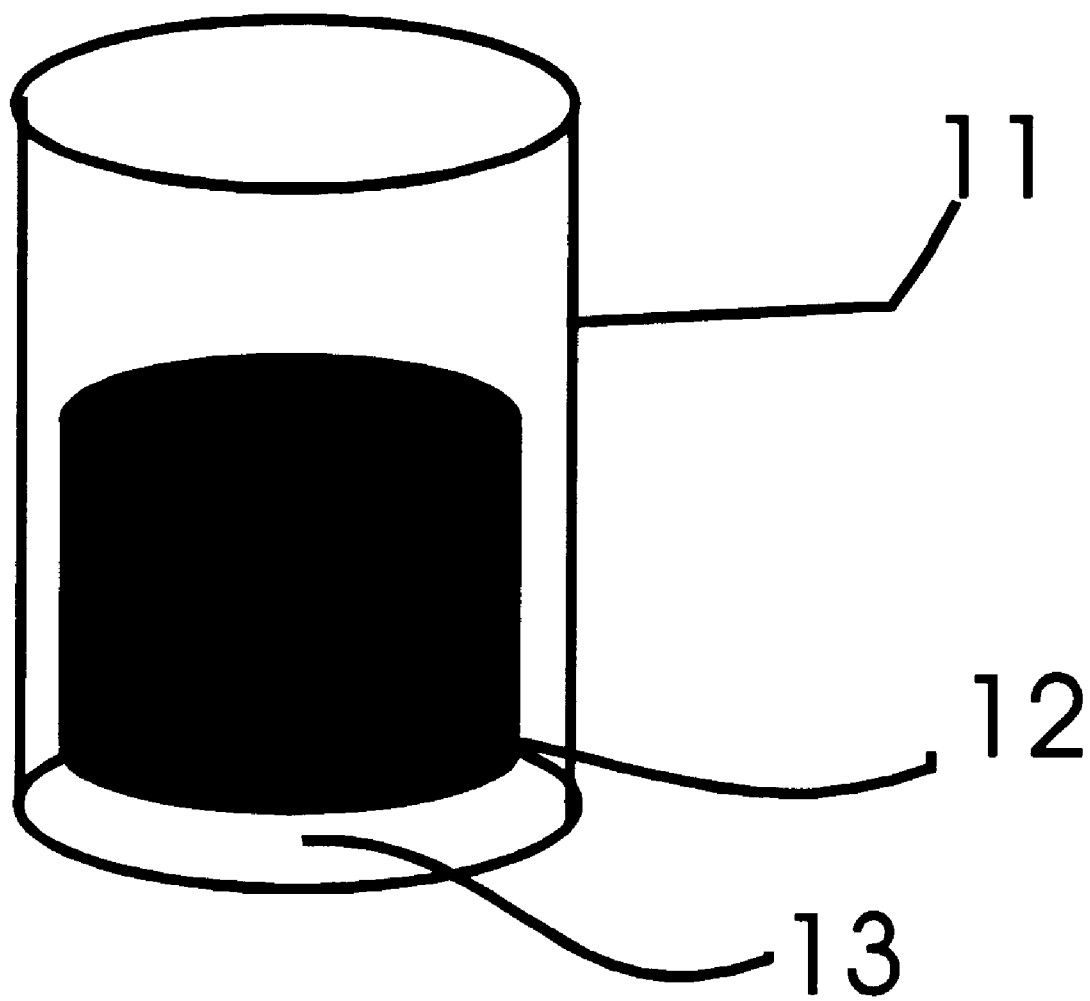
FIG. 6 is an expanded view of a container that can be centrifuged.

FIG. 6 shows a spin container (11) with a small piece of coomassie blue polymer material (12) in it. In this method, the protein sample is placed on top of said polymer material in a spin container. The presence of a fritte (13) at the bottom of said spin container prevents the polymer material from passing through while the protein solution will pass through said material and fritte. This protein solution will become stained by extracting the dye from the polymer material and can be collected in a collecting tube for qualitative and quantitative analysis.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, but is defined by the appended claims.

What is claimed is:

1. A de-staining system for electrophoresis gels for de-staining of excess dye from a stained gel, comprising a container containing a de-staining solution and a foam pad made of a material capable of absorbing the said dye with a capacity to de-stain said gel.

2. A de-staining system as described in claim 1, wherein said dye is selected from he group consisting of Coomassie blue, Commasie blue deriatives, Orange G. Brom cresol green or any other dye that binds to proteins.

3. A de-staining system as described in claim 1, wherein said foam pad is made of polyvinyl alcohol or its derivatives.

4. A de-staining system as described in claim 1, further comprises a magnet or magnetic material inside the said foam pad to agitate said de-staining solution by movement of said foam.

5. A de-staining system as described in claim 1, wherein said foam pad is affixed to the bottom of the said container.

6. A de-staining system as described in claim 1, further comprises a bag made by folding the said foam pad and said bag containing a de-staining material selected from the group consisting of charcoal, ion exchange resin or other materials that can absorb the dye.

* * * * *